US010369550B2

(12) United States Patent
Edulji et al.

(10) Patent No.: US 10,369,550 B2
(45) Date of Patent: Aug. 6, 2019

(54) CATALYST SYSTEM AND PROCESS FOR THE PRODUCTION OF GLYCOLS

(71) Applicant: SHELL OIL COMPANY, Houston, TX (US)

(72) Inventors: Smita Edulji, Houston, TX (US); Evert Van Der Heide, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/776,863

(22) PCT Filed: Nov. 17, 2016

(86) PCT No.: PCT/EP2016/078071
§ 371 (c)(1),
(2) Date: May 17, 2018

(87) PCT Pub. No.: WO2017/085222
PCT Pub. Date: May 26, 2017

(65) Prior Publication Data
US 2018/0339287 A1 Nov. 29, 2018

(30) Foreign Application Priority Data
Nov. 19, 2015 (EP) ..................................... 15195494

(51) Int. Cl.
| | |
|---|---|
| C07C 29/00 | (2006.01) |
| B01J 23/00 | (2006.01) |
| B01J 23/89 | (2006.01) |
| B01J 23/68 | (2006.01) |
| B01J 25/02 | (2006.01) |
| B01J 27/188 | (2006.01) |
| C07C 29/132 | (2006.01) |
| C07C 29/60 | (2006.01) |
| B01J 35/00 | (2006.01) |
| B01J 23/40 | (2006.01) |
| B01J 23/56 | (2006.01) |
| B01J 23/74 | (2006.01) |

(52) U.S. Cl.
CPC ............ B01J 23/892 (2013.01); B01J 23/40 (2013.01); B01J 23/56 (2013.01); B01J 23/687 (2013.01); B01J 23/74 (2013.01); B01J 25/02 (2013.01); B01J 27/188 (2013.01); B01J 35/0006 (2013.01); C07C 29/132 (2013.01); C07C 29/60 (2013.01); B01J 2231/643 (2013.01); Y02P 20/52 (2015.11)

(58) Field of Classification Search
CPC ............................ B01J 23/892; C07C 29/132
See application file for complete search history.

(56) References Cited

U.S. PATENT DOCUMENTS

| 7,759,280 B2 * | 7/2010 | Castellano ......... B01D 53/9418 502/305 |
|---|---|---|
| 2011/0046419 A1 | 2/2011 | Zhang et al. |
| 2011/0312487 A1 | 12/2011 | Chen et al. |
| 2012/0172633 A1 | 7/2012 | Zhang et al. |

FOREIGN PATENT DOCUMENTS

| CN | 103731258 A | 4/2014 |
|---|---|---|
| WO | 2013015955 A2 | 1/2013 |
| WO | 2015028398 A1 | 3/2015 |

OTHER PUBLICATIONS

Yu et al. Rapid microdetermination of carbon and hydrogen in organic compounds—use of silver tungstate (Ag2WO4)—magnesium oxide/cobalt oxide (Co3O4)/ silver tungstate (Ag2WO4)—magnesium oxide as the combustion tube packing. 9 (2), 131-136. HCAPLUS abstract. (Year: 1981).*
International Search Report and Written Opinion received for PCT Patent Application No. PCT/EP2016/078071, dated Jan. 19, 2017, 12 pages.
Ji et al., "Catalytic conversion of cellulose into ethylene glycol over supported carbide catalysts", Catalysis Today, vol. 147, issue No. 2, Sep. 30, 2009, pp. 77-85, XP026470036.
Liu et al., "Tungsten trioxide promoted selective conversion of cellulose into propylene glycol and ethylene glycol on a ruthenium catalyst", Angewandte Chemie International Edition, vol. 51, issue No. 13, pp. 3249-3253, XP055103283.
Ji et al., "Direct Catalytic Conversion of Cellulose into Ethylene Glycol Using Nickel-Promoted Tungsten Carbide Catalysts", Angew. Chem. Int. Ed, 2008, vol. 47, issue No. 44, pp. 8510-8513.
Zhang et al., "Kinetic study of retro-aldol condensation of glucose to glycolaldehyde with ammonium metatungstate as the catalyst", AIChE Journal, 2014, vol. 60, issue No. 11, pp. 3804-3813.

* cited by examiner

Primary Examiner — Sikarl A Witherspoon

(57) ABSTRACT

The invention provides a catalyst system comprising: a) one or more silver tungstate-containing species; and b) one or more catalytic species suitable for hydrogenation, wherein the weight ratio of said one or more silver tungstate-containing species to the one or more catalytic species suitable for hydrogenation is greater than 2.5:1, on the basis of the total weight of the catalyst system; and a process for the preparation of monoethylene glycol from starting material comprising one or more saccharides, by contacting said starting material with hydrogen in a reactor at a reactor temperature in the range of from 145 to 190° C. in the presence of a solvent and said catalyst system.

12 Claims, 1 Drawing Sheet

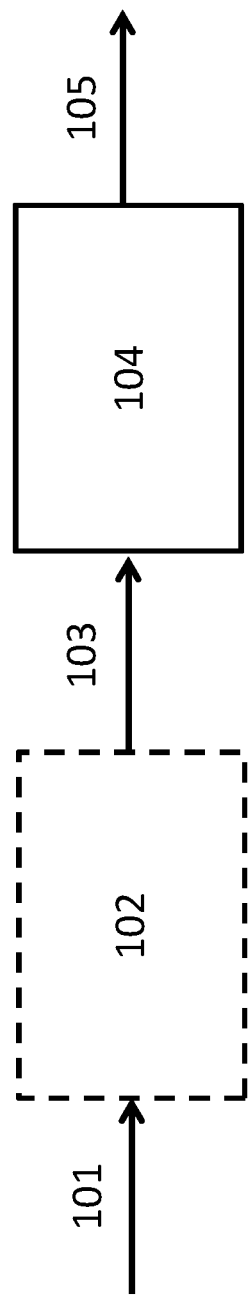

CATALYST SYSTEM AND PROCESS FOR THE PRODUCTION OF GLYCOLS

CROSS REFERENCE TO RELATED APPLICATIONS

This is a national stage application of International application No. PCT/EP2016/078071, filed 17 Nov. 2016, which claims benefit of priority of European application No. 15195494.8, filed 19 Nov. 2015.

FIELD OF THE INVENTION

The present invention relates to a process for the production of glycols, in particular monoethylene glycol and monopropylene glycol from a saccharide-containing feedstock.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers such as polyethylene terephthalate (PET).

Said glycols are currently made on an industrial scale by hydrolysis of the corresponding alkylene oxides, which are the oxidation products of ethylene and propylene, generally produced from fossil fuels.

In recent years increased efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. Current methods for the conversion of saccharides to glycols revolve around a hydrogenation/hydrogenolysis process.

Reported processes generally require a first catalytic species to perform the hydrogenolysis reaction, which is postulated to have a retro-aldol mechanism, and a second catalytic species for hydrogenation.

Processes for the conversion of cellulose to products including MEG are described in Angew. Chem. Int. Ed. 2008, 47, 8510-8513 and Catalysis Today 147 (2009), 77-85 using nickel-promoted tungsten carbide catalysts.

US 2011/0312487 A1 describes a process for generating at least one polyol from a saccharide-containing feedstock and a catalyst system for use therein, wherein said catalyst system comprises a) an unsupported component comprising a compound selected from the group consisting of a tungsten compound, a molybdenum compound and any combination thereof; and b) a supported compound comprising an active metal component selected from the group consisting of Pt, Pd, Ru, Rh, Ni, Ir, and combinations thereof on a solid catalyst support.

Examples of the unsupported catalyst component in US 2011/0312487 A1 are said to include tungstic acid ($H_2WO_4$), ammonium tungstate (($NH_4)_{10}H_2(W_2O_7)_6$), ammonium metatungstate (($NH_4)_6H_2(W_{12}O_{40})\cdot xH_2O$), ammonium paratungstate (($NH_4)_{10}[H_2W_{12}O_{42}]\cdot 4H_2O$), and tungstate, metatungstate and paratungstate compounds comprising at least Group I or II element.

Catalyst systems tested in US 2011/0312487 A1 utilise tungstic acid, tungsten oxide ($WO_2$), phosphotungstic acid ($H_3PW_{12}O_{40}$) and ammonium metatungstate as the unsupported catalyst component in conjunction with various nickel, platinum and palladium supported catalyst components.

US 2011/03046419 A1 describes a method for producing ethylene glycol from a polyhydroxy compound such as starch, hemicellulose, glucose, sucrose, fructose and fructan in the presence of catalyst comprising a first active ingredient and a second active ingredient, the first active ingredient comprising a transition metal selected from iron, cobalt, nickel, ruthenium, rhodium, palladium, iridium, and platinum, or a mixture thereof; the second active ingredient comprising a metallic state of molybdenum and/or tungsten, or a carbide, nitride, or phosphide thereof.

Angew. Chem. Int. Ed. 2012, 51, 3249-3253 describes a process for the selective conversion of cellulose into ethylene glycol and propylene glycol in the presence of a ruthenium catalyst and tungsten trioxide ($WO_3$).

AIChE Journal, 2014, 60 (11), pp. 3804-3813 describes the retro-aldol condensation of glucose using ammonium metatungstate as catalyst.

Continuous processes for generating at least one polyol from a saccharide-containing feedstock are described in WO 2013/015955 A, CN 103731258 A and WO 2015/028398 A1.

The products of the afore-mentioned processes are typically a mixture of materials comprising MEG, MPG, 1,2-butanediol (1,2-BDO) and other by-products.

The reactor temperature selected in processes for the conversion of saccharide-containing feedstocks to glycols depends upon the nature of the saccharide-containing feedstock and is typically selected to achieve a good balance of retro-aldol activity which is favoured at higher temperatures and hydrogenation which is favoured at lowered temperatures.

Generally, said processes are typically performed at reactor temperatures within the range of from 195 to 245° C.

For example, when glucose is the starting saccharide, then typical reactor temperatures are in the range of from 195 to 230° C. When lower temperatures are employed, the sorbitol by-product yield from the hydrogenation of glucose increases and the yield of glycols decreases.

In order to effect energy savings, it is highly desirable to be able to utilise lower reactor temperatures without adversely affecting the yield of product glycols in the conversion of saccharide-containing feedstocks. Other benefits of lower reactor temperature include less of the starting material being converted to by-products and so there is a potential to further increase glycol yields. Another advantage would be to be able to operate at a lower hydrogen pressure as hydrogenation is favoured at lower temperature. Furthermore, lower temperature operation would also potentially result in lower metallurgy corrosion rates.

SUMMARY OF THE INVENTION

The present invention has surprisingly found that certain catalyst systems may be utilised at lower reactor temperatures whilst still displaying advantageous performance in the conversion of saccharide-containing feedstocks to polyols.

Accordingly, in a first aspect, the present invention there is provided a catalyst system comprising:
a) one or more silver tungstate-containing species; and
b) one or more catalytic species suitable for hydrogenation, wherein the weight ratio of said one or more silver tungstate-containing species to the one or more catalytic species suitable for hydrogenation is greater than 2.5:1, on the basis of the total weight of the catalyst system.

In a second aspect, the present invention provides a process for the preparation of monoethylene glycol from starting material comprising one or more saccharides, by contacting said starting material with hydrogen in a reactor at a reactor temperature in the range of from 145 to 190° C. in the presence of a solvent and said catalyst system.

BRIEF DESCRIPTION OF THE DRAWINGS

FIG. 1 is a schematic diagram of an exemplary, but non-limiting, embodiment of the process of the invention.

DETAILED DESCRIPTION OF THE INVENTION

In the present invention, there has been surprisingly found a catalyst system which gives rise to advantageous yields of ethylene glycol and propylene glycol from saccharide-containing feedstocks at low reactor temperatures in the range of from 145 to 190° C.

In particular, the present invention has found that by utilising a catalyst system comprising increased amounts of silver tungstate-containing species to catalyse hydrogenolysis in combination with one or more catalytic species suitable for hydrogenation, it is surprisingly possible to operate at lower reactor temperatures than are typically used in the conversion of saccharide-containing feedstocks to polyols, whilst still achieving advantageous product yields.

The one or more catalytic species present in the catalyst system which are suitable for hydrogenation of material present in the reactor may be present in elemental form or as one or more compounds. It is also suitable that these one or more catalytic species may be present in chemical combination with one or more other ingredients in the catalyst system.

The one or more catalytic species which are suitable for the hydrogenation are not limited and may be conveniently selected from one or more transition metals from Groups 8, 9 or 10 of the Periodic Table, and compounds thereof. Preferably, said catalytic species may be one or more transition metals selected from the group of cobalt, iron, platinum, palladium, ruthenium, rhodium, nickel, iridium, and compounds thereof.

In one embodiment of the present invention, the one or more catalytic species suitable for hydrogenation are solid, unsupported species. Examples of such species include Raney Ni.

In another embodiment of the present invention, the one or more catalytic species suitable for hydrogenation are in homogeneous form.

In yet another embodiment of the present invention, the one or more catalytic species suitable for hydrogenation are on one or more solid catalyst supports.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers.

Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In the catalyst system of the present invention, the one or more silver tungstate-containing species may be present in the catalyst system in unsupported form or, alternatively, may also be present on an inert support. Examples of suitable supports include, but are not limited to aluminas, silicas, zirconium oxide, magnesium oxide, zinc oxide, titanium oxide, carbon, activated carbon, zeolites, clays, silica alumina and mixtures thereof.

In the catalyst system of the present invention, the weight ratio of the one or more silver tungstate-containing species to the one or more catalytic species suitable for hydrogenation is preferably greater than 3:1, more preferably greater than 4:1 on the basis of the total weight of the catalyst system.

The present invention further provides a process for the preparation of monoethylene glycol from starting material comprising one or more saccharides, by contacting said starting material with hydrogen in a reactor at a reactor temperature in the range of from 145 to 190° C. in the presence of a solvent and a catalyst system as hereinbefore described.

In one embodiment of the present invention, the one or more silver tungstate-containing species are present as the catalytic species suitable for hydrogenolysis in the reaction mixture in an amount in the range of from 0.005 to 10 wt. %, preferably in the range of from 0.005 to 8 wt. %, more preferably in the range of from 0.01 to 6 wt. %, based on the total weight of the reaction mixture.

By "reaction mixture" in the present invention is meant the total weight of the starting material, catalyst system, hydrogen, solvent present in the reactor. The starting material for use in the process of the present invention comprises one or more saccharides selected from the group consisting of monosaccharides, disaccharides, oligosaccharides and polysaccharides. Examples of polysaccharides include cellulose, hemicelluloses, starch, glycogen, chitin and mixtures thereof. If the starting material comprises oligosaccharides or polysaccharides, then, optionally, said starting material may be subjected to a pre-treatment before being fed to the reactor in a form that can be more conveniently converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the starting material for use in the process of the present invention comprises one or more saccharides selected from the group consisting of glucose, sucrose and starch. Said saccharides are suitably present as a solution, a suspension or a slurry in solvent.

The solvent present in the reactor may be conveniently selected from water, $C_1$ to $C_6$ alcohols, ethers and other suitable organic compounds, and mixtures thereof. Preferably, the solvent is water. If the starting material is provided to the reactor as a solution, suspension or slurry in a solvent, said solvent is also suitably water or a $C_1$ to $C_6$ alcohols, ethers and other suitable organic compounds, or mixtures thereof. Preferably, both solvents are the same. More preferably, both solvents comprise water. Most preferably, both solvents are water.

The temperature in the reactor is generally in the range of from 145 to 190° C., preferably in the range of from 150 to 190° C., more preferably in the range of from 150 to 185° C. and most preferably in the range of from 155 to 185° C.

Preferably, the reactor is heated to a temperature within these limits before addition of any starting material and is maintained at such a temperature until all reaction is complete.

The pressure in the reactor is generally at least 1 MPa, preferably at least 2 MPa, more preferably at least 3 MPa. The pressure in the reactor is generally at most 25 MPa, more preferably at most 20 MPa, more preferably at most 18 MPa. Preferably, the reactor is pressurised to a pressure within these limits by addition of hydrogen before addition of any starting material and is maintained at such a pressure until all reaction is complete. This can be achieved by subsequent addition of hydrogen.

The process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents. It may also be suitable to add further hydrogen to the reactor as the reaction proceeds.

The reactor in the present invention may be any suitable reactor known in the art.

The process may be carried out as a batch process or as a continuous flow process.

In one embodiment of the invention, the process is a batch process. In such a process, the reactor may be loaded with the catalyst system, solvent and one or more saccharides, and the reactor may then be purged and pressurized with hydrogen at room temperature, sealed and heated to the reaction temperature.

In embodiments of the invention, addition of further portions of starting material may occur in a continuous manner or the portions may be added in a discontinuous manner with time elapsing between the end of the addition of one portion and the start of the addition of the next portion. In the embodiment of the invention wherein the portions are added in a discontinuous manner, the number and size of each portion will be dependent on the scale of the reactor. Preferably, the total number of portions including the first portion is no less than 5, more preferably no less than 8, even more preferably no less than 10. The amount of time over which each portion is added and the time to be elapsed between the end of the addition of one portion and the start of the addition of the next portion will also depend on the scale of the reactor. Preferably, the time to be elapsed between the end of the addition of one portion and the start of the addition of the next portion will be greater than the amount of time over which each portion is added. In embodiments of the invention, wherein the process is a batch process, after addition of all of the portions of the starting material, the reaction may then be allowed to proceed to completion for a further period of time. The reaction product will then be removed from the reactor.

In embodiments of the invention wherein the process is carried out as a continuous flow process, after initial loading of some or all of the catalysts and, optionally, solvent, the reactor pressurised with hydrogen and heated, and then the first portion of starting material is introduced into the reactor and allowed to react. Further portions of starting material are then provided to the reactor. Reaction product is removed from the reactor in a continuous manner. In some embodiments of the invention, catalysts may be added in a continuous fashion.

In embodiments of the present invention, the starting material is suitably a saccharide feedstock comprising at least 1 wt. % saccharide as a solution, suspension or slurry in a solvent. Preferably, said saccharide feedstock comprises at least 2 wt. %, more preferably at least 5 wt. %, even more preferably at least 10 wt. %, most preferably at least 20 wt. % saccharide in a solvent. Suitably, the saccharide feedstock contains no more than 50 wt. %, preferably no more than 40 wt. % saccharide in a solvent.

The weight ratio of the catalyst system to saccharides in the starting material is suitably in the range of from 1:100 to 1:10000.

FIG. 1 is a schematic diagram of an exemplary, but non-limiting, embodiment of the process of the invention. A feed 101 comprising polysaccharides and solvent is provided to a pre-treatment unit 102 to convert it mainly into glucose, sucrose and/or starch in solvent to form feed 103. The pre-treatment unit 102 may consist of multiple pre-treatment units performing the same or different pre-treatment functions. Pre-treatment is an optional step in case the feed is polysaccharide. Feed 103 is then fed to the main reactor 104 where it undergoes hydrogenation/hydrogenolysis in the presence of catalysts to produce a product stream comprising of MEG 105.

The process of the present invention is not limited to any particular reactor or flow configurations, and those depicted in FIG. 1 are merely exemplary. Furthermore, the sequence in which various feed components are introduced into the process and their respective points of introduction, as well as the flow connections, may be varied from that depicted in FIG. 1.

The invention is further illustrated by the following Examples.

EXAMPLES 75 ml Hastelloy C batch autoclaves, with magnetic stir bars, were used for the experiments. In typical experiments, known weights of catalysts and feedstocks were added to the autoclaves along with 30 ml of the solvent (typically water). If the catalysts or feedstocks were present as slurries or solutions, the total volume of those as well as the solvent was kept at 30 ml.

Methodology

In Example 1, 0.3 g of glucose was dissolved in 30 ml of water. The loaded autoclave was then purged three times with nitrogen, followed by hydrogen purge. The hydrogen pressure was then raised to 2000 psig or ~14 MPa of hydrogen and the autoclave was sealed and left stirring overnight to do a leak test.

The next morning the autoclave was de-pressurised to the target hydrogen pressure (1450 psig or 10.1 MPa) at room temperature, and closed. Next the temperature was ramped to the target run temperature either as a fast ramp or in steps.

In Example 1, there was a fast ramp to temperature. The autoclave was held at the target temperature for known durations of time (75 min), while both the temperature and pressure were monitored. After the required run time had elapsed, the heating was stopped, and the reactor was cooled down to room temperature, de-pressurised, purged with nitrogen and then opened.

The contents of the autoclave were then analyzed via Gas Chromatography (GC) or High Pressure Liquid Chromatography (HPLC) after being filtered.

Table 1 provides details on the catalyst systems tested in Example 1.

Catalyst system B (catalysts B-1 to B-3) is comparative in nature. In addition, catalyst A-1 is also comparative in nature. Catalysts A-2 and A-3 are according to the present invention.

TABLE 1

| Catalyst System | Catalyst No. | Hydrogenolysis Catalyst (a) | | | Hydrogenation Catalyst (b) | | Ratio (a):(b) |
|---|---|---|---|---|---|---|---|
| | | Component | Amount (g) | W content (g) | Component | Amount (g) | |
| A Silver tungstate/ Raney Ni | A-1 (comp.) | Silver tungstate | 0.0417 | 0.017 | Raney Ni 2800 | 0.020 | 2.1 |
| | A-2 | Silver tungstate | 0.0834 | 0.033 | Raney Ni 2800 | 0.020 | 4.2 |
| | A-3 | Silver tungstate | 0.1251 | 0.05 | Raney Ni 2800 | 0.020 | 6.3 |
| B Sodium phospho- tungstate/ Raney Ni | B-1 (comp.) | Sodium phospho- tungstate | 0.0150 | 0.011 | Raney Ni 2800 | 0.010 | 1.5 |
| | B-2 (comp.) | Sodium phospho- tungstate | 0.0450 | 0.033 | Raney Ni 2800 | 0.010 | 4.5 |
| | B-3 (comp.) | Sodium phospho- tungstate | 0.0600 | 0.044 | Raney Ni 2800 | 0.010 | 6 |
| | B-4 (comp.) | Sodium phospho- tungstate | 0.0900 | 0.067 | Raney Ni 2800 | 0.010 | 9 |

Results

In the tables of results herein, MEG=monoethylene glycol, MPG=monopropylene glycol, HA=hydroxyacetone, 1,2-BDO=1,2-butanediol and 1H2BO=1-hydroxy-2-butanone.

Example 1

Table 2 presents the gas chromatography (GC) results of testing comparative catalyst A-1 at various temperatures.

TABLE 2

| Temperature °C. | MEG wt. % | MPG wt. % | HA* wt. % | 1,2-BDO** wt. % | 1H2BO*** wt. % | MEG: (MPG + HA) |
|---|---|---|---|---|---|---|
| 230 | 39.4 | 9.5 | 0.8 | 6.9 | 1.4 | 3.8 |
| 195 | 37.7 | 6.2 | 1.0 | 4.1 | 1.4 | 5.2 |
| 180 | 31.2 | 5.1 | 0.8 | 3.3 | 1.1 | 5.3 |
| 160 | 18.4 | 4.5 | 0.0 | 1.4 | 0.7 | 4.1 |

* hydroxyacetone
** 1,2-butanediol
*** 1-hydroxy-2-butanone

It is apparent from Table 2 that as the reactor temperature is decreased from 230 to 160° C., the yield of MEG and the total yield of (MEG+MPG) decreases.

Example 2

Table 3 presents the GC results of testing comparative catalyst B-2 comprising sodium phosphotungstate as the hydrogenolysis catalyst component and Raney Ni as the hydrogenation catalyst component.

TABLE 3

| Temperature °C. | MEG wt. % | MPG wt. % | HA* wt. % | 1,2-BDO** wt. % | 1H2BO*** wt. % | MEG: (MPG + HA) |
|---|---|---|---|---|---|---|
| 195 | 34.9 | 4.6 | 2.4 | 3.1 | 3.6 | 5.0 |
| 160 | 9.0 | 4.3 | 0.4 | 0.0 | 0.8 | 1.9 |

* hydroxyacetone
** 1,2-butanediol
*** 1-hydroxy-2-butanone

It is apparent from Table 3 that when comparative catalyst B-2 moved from a reactor temperature of 195° C. to a lower temperature of 160° C., there was a large decrease in the amount of MEG produced and also a significant drop in the ratio of MEG:(MPG+HA).

Example 3

Table 4 presents the GC results of testing various comparative catalyst systems comprising sodium phosphotungstate as the hydrogenolysis catalyst component and Raney Ni as the hydrogenation catalyst component at 160° C.

It is apparent that increasing the ratio of sodium phosphotungstate to hydrogenation catalyst in catalyst system B has no positive effect on the catalyst performance. That is to say, the results for catalyst systems B-1, B-2, B-3 and B-4 are all poor at low reactor temperatures of 160° C.

TABLE 4

| Catalyst No. | Hydrogenolyis Catalyst (a) | | | Hydrogenation Catalyst (b) | | Ratio (a):(b) | MEG wt. % | MPG wt. % | HA* wt. % | 1,2-BDO** wt. % | 1H2BO*** wt. % | MEG: (MPG + HA) |
|---|---|---|---|---|---|---|---|---|---|---|---|---|
| | Component | Amount g | W content g | Component | Amount g | | | | | | | |
| B-1 (comp.) | Sodium phospho- tungstate | 0.015 | 0.011 | Raney Ni 2800 | 0.01 | 1.5 | 10.3 | 4.3 | 1.1 | 2.7 | 1.3 | 1.9 |
| B-2 (comp.) | Sodium phospho- tungstate | 0.045 | 0.033 | Raney Ni 2800 | 0.01 | 4.5 | 9.0 | 4.3 | 0.4 | 0.0 | 0.8 | 1.9 |
| B-3 | Sodium | 0.06 | 0.044 | Raney Ni | 0.01 | 6 | 5.9 | 4.3 | 0.0 | 0.0 | 0.0 | 1.4 |

TABLE 4-continued

| Catalyst No. | Hydrogenolyis Catalyst (a) Component | Amount g | W content g | Hydrogenation Catalyst (b) Component | Amount g | Ratio (a):(b) | MEG wt. % | MPG wt. % | HA* wt. % | 1,2-BDO** wt. % | 1H2BO*** wt. % | MEG: (MPG + HA) |
|---|---|---|---|---|---|---|---|---|---|---|---|---|
| (comp.) | phospho-tungstate | | | 2800 | | | | | | | | |
| B-4 (comp.) | Sodium phospho-tungstate | 0.09 | 0.067 | Raney Ni 2800 | 0.01 | 9 | 6.8 | 4.3 | 0.0 | 0.0 | 0.3 | 1.6 |

\* hydroxyacetone
\*\* 1,2-butanediol
\*\*\* 1-hydroxy-2-butanone

Example 4

Catalyst system A comprises a combination of silver tungstate as hydrogenolysis catalyst (a) and Raney Ni as hydrogenation catalyst (b), in varying amounts.

Table 5 presents the results of testing different ratios of said catalyst components in catalyst system A at a temperature of 180° C. for a run time of 75 minutes.

It is apparent from Table 5 that catalysts A-2 and A-3 perform much better than comparative catalyst A-1 at lower temperatures of 180° C. This clearly shows that by increasing the amount of hydrogenolysis catalyst in the catalyst system, high yields can also be obtained at lower temperatures.

TABLE 5

| Catalyst No. | Temp. ° C. | MEG wt. % | MPG wt. % | HA* wt. % | 1,2-BDO** wt. % | 1H2BO*** wt. % | MEG: (MPG + HA) |
|---|---|---|---|---|---|---|---|
| A-1 (comp.) | 180 | 31.2 | 5.1 | 0.8 | 3.3 | 1.1 | 5.3 |
| A-2 | 180 | 35.4 | 5.6 | 0.9 | 3.6 | 1.3 | 5.5 |
| A-3 | 180 | 42.4 | 7.9 | 5.0 | 5.7 | 7.1 | 3.3 |

\* hydroxyacetone
\*\* 1,2-butanediol
\*\*\* 1-hydroxy-2-butanone

Example 5

Catalyst system A comprises a combination of silver tungstate as hydrogenolysis catalyst (a) and Raney Ni as hydrogenation catalyst (b), in varying amounts.

Table 6 presents the results of testing different ratios of said catalyst components in catalyst system A at 160° C. for a run time of 75 minutes. Catalyst system A comprises a combination of silver tungstate and Raney Ni in varying amounts.

It is apparent from Table 6 that catalysts A-2 and A-3 perform much better than comparative catalyst A-1 at lower temperatures of 160° C. Again, this clearly shows that by increasing the amount of hydrogenolysis catalyst in the catalyst system, high yields can also be obtained at lower temperatures.

Indeed, by comparison of the results in Tables 2 and 6, it is of note that the yield of MEG using catalyst A-3 at 160° C. exceeds the yield of MEG obtained by using catalyst A-1 at a higher temperature of 180° C.

Furthermore, catalyst A-3 not only shows good yields of MEG in testing runs at 160° C. reactor temperature, but also shows very high C2:C3 ratios (MEG:(MPG+HA)) under said low temperature.

TABLE 6

| Catalyst No. | Temp. ° C. | MEG wt. % | MPG wt. % | HA* wt. % | 1,2-BDO** wt. % | 1H2BO*** wt. % | MEG: (MPG + HA) |
|---|---|---|---|---|---|---|---|
| A-1 (comp.) | 160 | 18.4 | 4.5 | 0.0 | 1.4 | 0.7 | 4.1 |
| A-2 | 160 | 25.9 | 4.5 | 1.4 | 2.8 | 1.7 | 4.4 |
| A-3 | 160 | 34.4 | 4.7 | 2.2 | 3.1 | 3.1 | 5.0 |

\* hydroxyacetone
\*\* 1,2-butanediol
\*\*\* 1-hydroxy-2-butanone

Discussion

Hitherto in the prior art, it has not been possible to obtain high glycol yields at lower temperatures.

However, it is evident from the results in the Examples herein that in the present invention it has been surprisingly found that by increasing the amount silver tungstate-containing species acting as hydrogenolysis catalyst in a catalyst system comprising said hydrogenolysis catalyst in combination with one or more catalytic species suitable for hydrogenation, the resulting catalyst system displays advantageous results in the preparation of monoethylene glycol from starting material comprising one or more saccharides at low reactor temperatures in the range of from 145 to 190° C. as compared to other catalyst systems.

That which is claimed is:

1. A process for the preparation of monoethylene glycol from starting material comprising one or more saccharides, by contacting said starting material with hydrogen in a reactor at a reactor temperature in the range of from 145 to 190° C. in the presence of a solvent and the catalyst system comprising:
    (a) one or more silver tungstate-containing species; and
    (b) one or more catalytic species suitable for hydrogenation, wherein the weight ratio of said one or more silver tungstate-containing species to the one or more catalytic species suitable for hydrogenation is greater than 2.5:1, on the basis of the total weight of the catalyst system.

2. The process according to claim 1, wherein the saccharides are selected from the group consisting of monosaccharides, disaccharides, oligosaccharides and polysaccharides.

3. The process according to claim 1, wherein the catalytic species suitable for hydrogenolysis in the catalyst system are present in an amount in the range of from 0.005 to 10 wt. %, based on the total weight of the reaction mixture.

4. The process according to claim 1, wherein the reactor temperature is in the range of from 150 to 185° C.

5. The process according to claim 1, wherein the reactor pressure is in the range of from at least 1 to at most 25 MPa.

6. The process according to claim 1, wherein the one or more catalytic species suitable for hydrogenation are selected from one or more transition metals from Groups 8, 9 or 10 of the Periodic Table, or compounds thereof.

7. The process according to claim 1, wherein the one or more catalytic species suitable for hydrogenation are selected from one or more transition metals selected from the group of cobalt, iron, platinum, palladium, ruthenium, rhodium, nickel, iridium, and compounds thereof.

8. The process according to claim 1, wherein the one or more catalytic species suitable for hydrogenation are solid, unsupported species.

9. The process according to claim 8, wherein the one or more catalytic species suitable for hydrogenation are on solid catalyst supports.

10. The process according to claim 1, wherein the solid catalyst support is selected aluminas, silicas, zirconium oxide, magnesium oxide, zinc oxide, titanium oxide, carbon, activated carbon, zeolites, clays, silica alumina and mixtures thereof.

11. The process according to claim 1, wherein the weight ratio of the one or more silver tungstate-containing species to the one or more catalytic species suitable for hydrogenation is greater than 3:1, on the basis of the total weight of the catalyst system.

12. The process according to claim 1, wherein the weight ratio of the one or more silver tungstate-containing species to the one or more catalytic species suitable for hydrogenation is greater than 4:1, on the basis of the total weight of the catalyst system.

\* \* \* \* \*